(12) United States Patent
Izzo

(10) Patent No.: US 12,036,095 B2
(45) Date of Patent: Jul. 16, 2024

(54) BARRIER BAND

(71) Applicant: Lorri Lynn Izzo, Sparta, NJ (US)

(72) Inventor: Lorri Lynn Izzo, Sparta, NJ (US)

(*) Notice: Subject to any disclaimer, the term of this patent is extended or adjusted under 35 U.S.C. 154(b) by 316 days.

(21) Appl. No.: 17/503,833

(22) Filed: Oct. 18, 2021

(65) Prior Publication Data

US 2023/0120123 A1 Apr. 20, 2023
US 2023/0255830 A9 Aug. 17, 2023

Related U.S. Application Data

(63) Continuation-in-part of application No. 16/537,922, filed on Aug. 12, 2019, now abandoned.

(51) Int. Cl.
*A61F 13/00* (2006.01)
*A61M 25/02* (2006.01)

(52) U.S. Cl.
CPC ....... *A61F 13/00017* (2013.01); *A61M 25/02* (2013.01); *A61F 2013/00097* (2013.01); *A61F 2013/00119* (2013.01); *A61F 2013/00153* (2013.01); *A61F 2013/00272* (2013.01); *A61M 2025/0206* (2013.01); *A61M 2025/0213* (2013.01)

(58) Field of Classification Search
CPC .... A61F 13/00017; A61F 2013/00272; A61M 2025/0206; A61M 2025/0246; A61M 2025/0213; A41D 13/08; A41D 13/055; A41D 20/00
See application file for complete search history.

(56) References Cited

U.S. PATENT DOCUMENTS

| | | | | |
|---|---|---|---|---|
| 5,752,633 A | * | 5/1998 | Antaki | A45F 5/00 224/222 |
| 2005/0020977 A1 | * | 1/2005 | Eldridge | A61M 25/02 604/111 |
| 2006/0074368 A1 | * | 4/2006 | Palma | A61F 15/008 602/42 |
| 2008/0045906 A1 | * | 2/2008 | Grissom | A61M 25/02 604/179 |
| 2019/0046772 A1 | * | 2/2019 | Jutras | A61M 25/02 |
| 2020/0129737 A1 | * | 4/2020 | Woodard | A61M 25/02 |

FOREIGN PATENT DOCUMENTS

CN 206391285 U * 8/2017
CN 108355187 A * 8/2018

* cited by examiner

*Primary Examiner* — Daniel J Colilla

(57) ABSTRACT

The Barrier Band for an area on a human body, involving a vascular device access area. The present invention relates to an apparatus that provides a barrier between a person's skin, and any vascular access device, and its components, to prevent compromising skin, and to provide comfort to a person.

The barrier band is offered in many sizes, and is made with a stretchable material, to accommodate every patient, and any body part being serviced. It is offered in both a washable and disposable version. Its design and stitching may vary, and it may or may not have an adjustable apparatus, or any other suitable component to tighten or loosen the band.

15 Claims, 10 Drawing Sheets

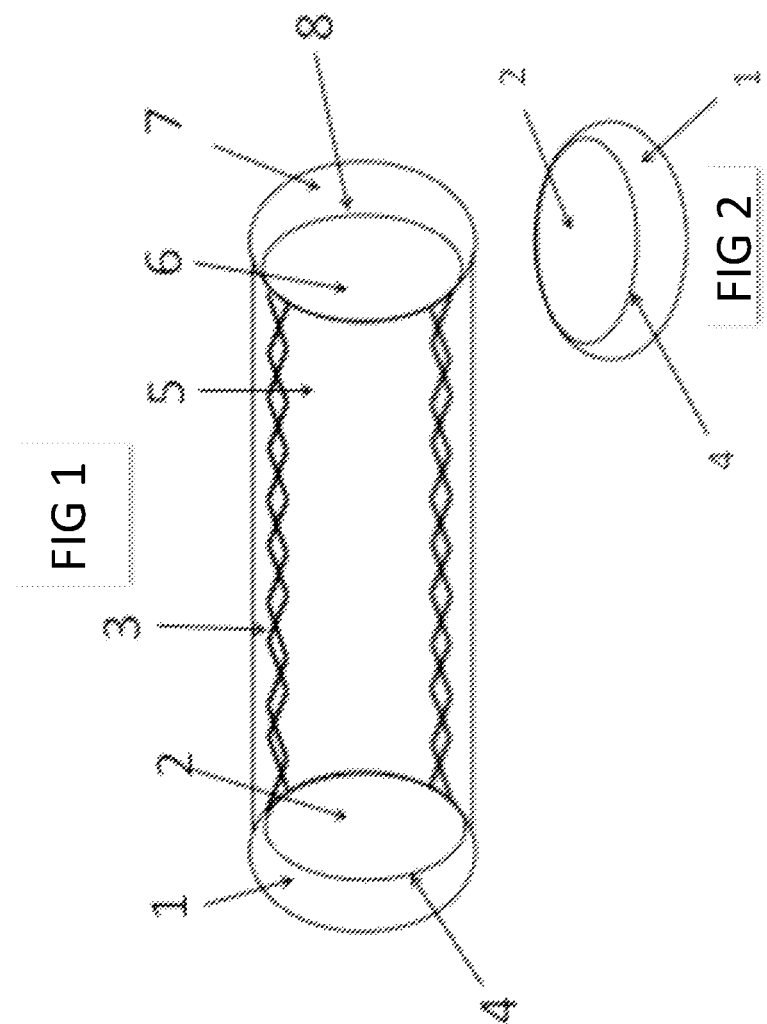

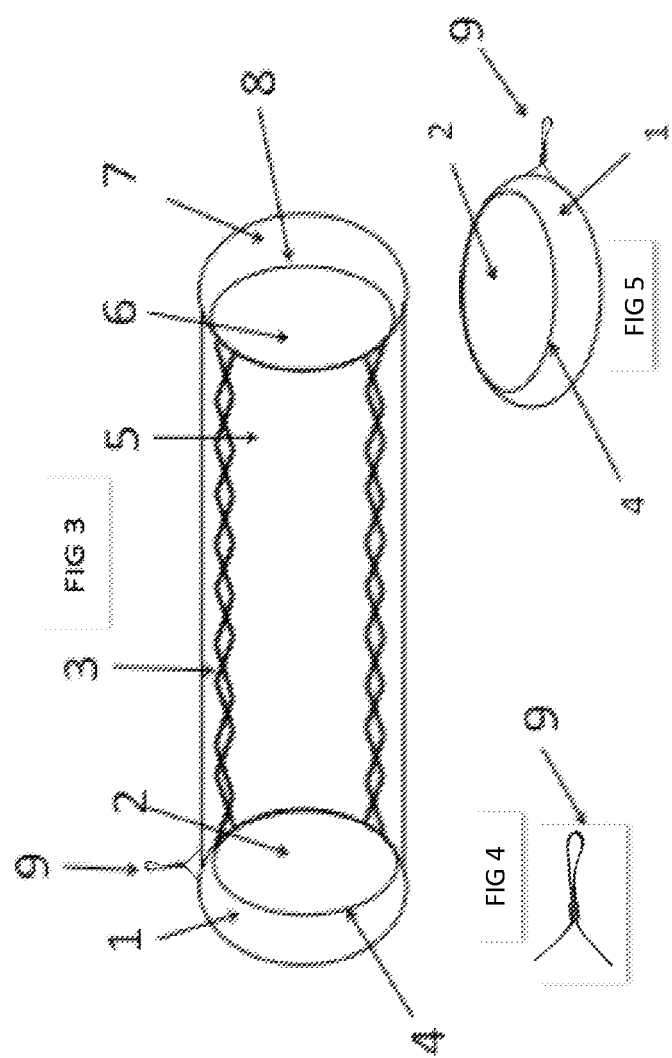

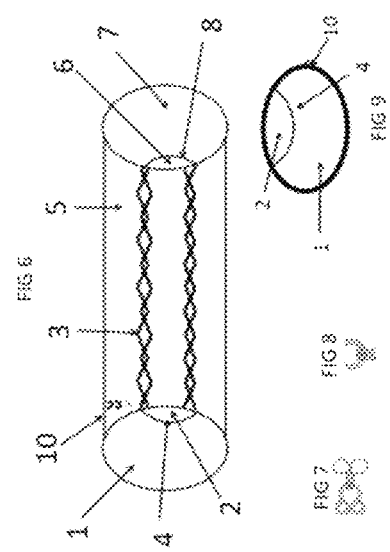

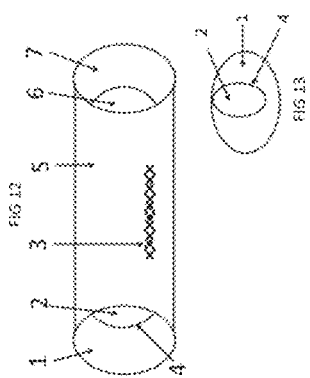

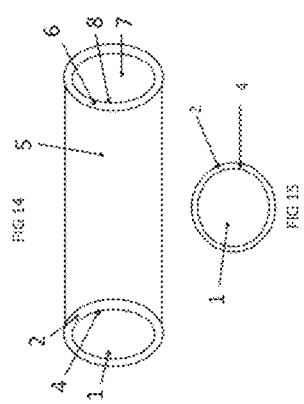

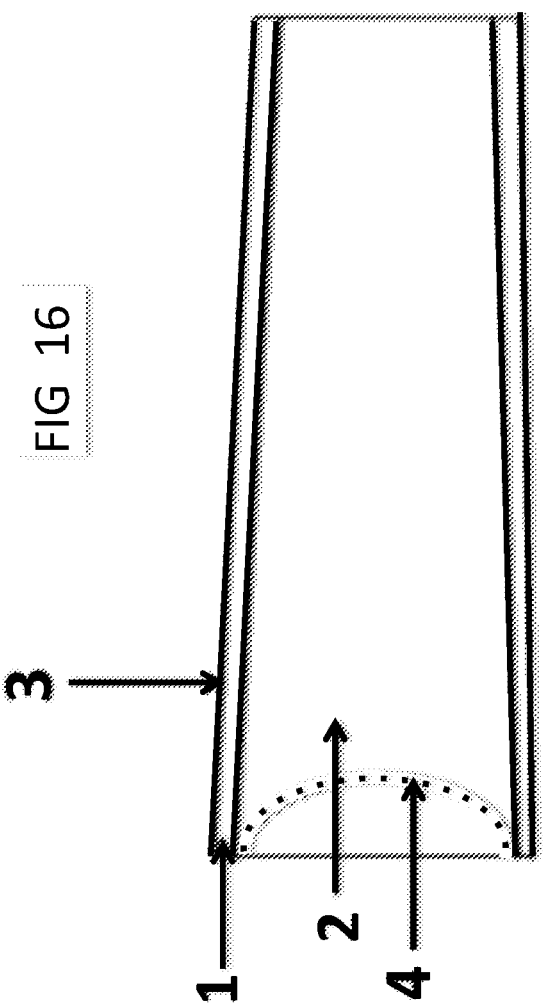

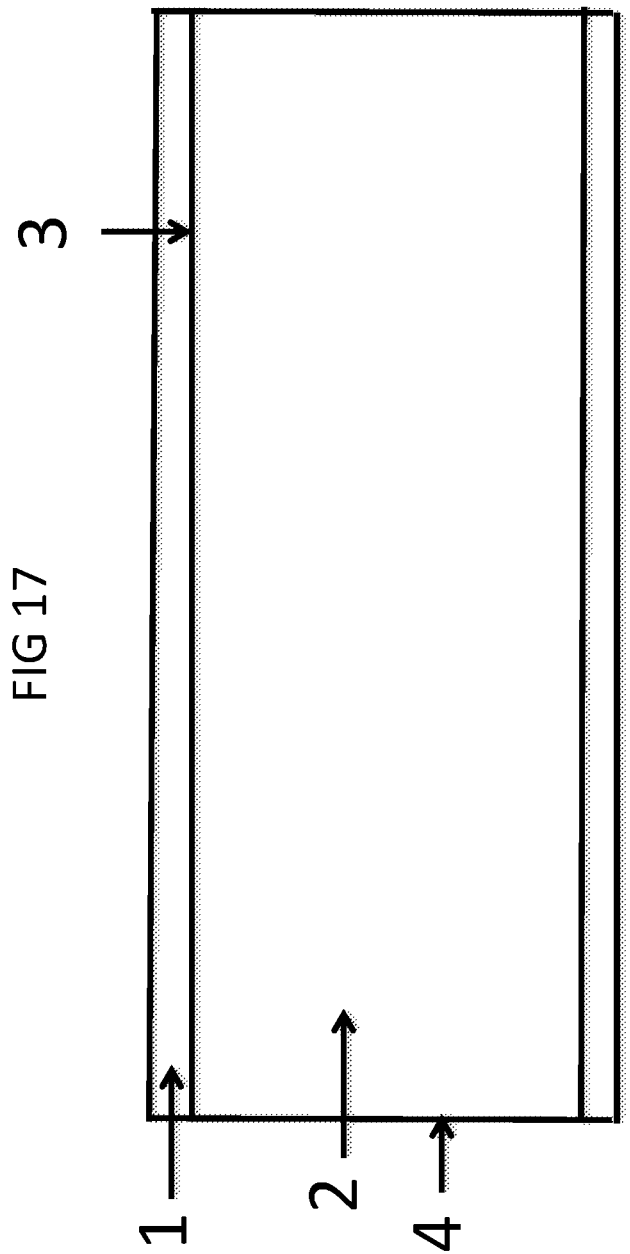

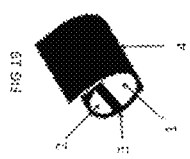
FIG. 19
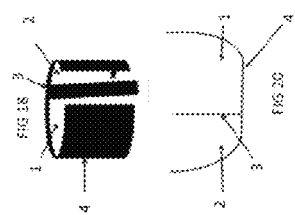
FIG. 18
FIG. 20

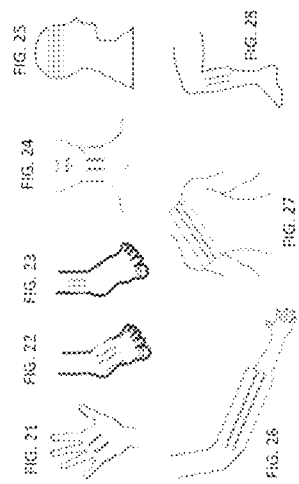

BARRIER BAND

CROSS-REFERENCE TO RELATED APPLICATIONS

The application is a continuation in part and claims the benefits of U.S. Non-Provisional application Ser. No. 16/537,922, filed Aug. 12, 2019.

BACKGROUND OF THE INVENTION

1. Field of Invention

This invention relates generally to a vascular access device site, and more specifically to a sleeve with which can assist in preventing such a site from compromising someone's skin. When a patient has any type of vascular access device is covered with medical grade gauze, netting, or other suitable material. This is to keep it secure. A problem that many patients have when they are required to wear this cover is that their skin becomes irritated as a result of the cover causing the vascular access device and its components to press against the skin. Consequently, whether it is short or long-term use, the skin should be protected during its use, and no current invention provides a barrier between the skin and vascular access device and its components, like the present invention does with its tunnel. At times patients that need this device already have comprised skin, which means it will be further compromised. This complete coverage fully eliminates all contact. The band's specific measurement and configuration is determined by a person's weight, and which body part it is utilized. A common complaint among people is that with extended use, a cover of this type does not work effectively. For that reason, the disposable and washable version are offered in a specific stretchable materials, and some washable variations of the Barrier Band have an adjustable apparatus including: zips, hooks, toggles, elastic, snaps, zippers, velcro, or any other suitable component present. This adjustable apparatus is implemented in an effort to tighten or loosen the band.

SUMMARY OF INVENTION

It is an object of the present invention to provide an easily installable means for protecting a vascular access device area on a human body. It is another object of the present invention to achieve this using multiple sizes, and further, using a stretchable material, in both the disposable and washable versions, allowing it to fit the various sizes of human extremities. These and other objects and advantages of the invention will become readily apparent as the following description is read in conjunction with the accompanying drawings. The present invention relates to a sleeve, sometimes referred to as a band, apparatus that provides a barrier with a tunnel, sometimes referred to as a ductway, between the skin on any part of a person's body and a vascular access device and its components. It is utilized to prevent skin from being compromised, eliminate discomfort, and keep the vascular access device and its components secure.

The Barrier Band is constructed in one of two ways. One way is a breathable, disposable mesh, gauze, netting or any other suitable disposable material. The other is a breathable, washable, polyester, spandex or any other suitable washable material. With usage and a person's weight fluctuation a person could need to tighten or loosen the Barrier Band, and that is why some versions offer built in adjustable apparatuses. There are several ways that the method of the barrier is delivered. The disposable version is changed frequently. This variant is determined by a person's weight, and where the sleeve will be located on their body. The sleeve in one embodiment has a tunnel opening on one end and at least another tunnel opening at the other end integrally formed in the sleeve, which form a barrier between the person's skin and any vascular access device and its is pliable, and components. This band's midsection contains stitching defining the tunnel. The sleeves cylindrical in shape, with two open ends. Another embodiment has the same features, and has only one stitch to secure the canal. The length of stitching on a Barrier Band can vary in size. Glue or any suitable material that could adhere the tunnel to the band can replace stitching. An area of the sleeve or stitching might be a different color to for instructional purposes. Another embodiment has containing no stitching, and is essentially a band within a band, acting as a double layer, still providing the barrier between the skin and vascular access device and its components. Another embodiment is flat opened version of the present invention, and involves a wrapping technique. The Barrier Band may or may not have an adjustable apparatus including: zips, hooks, toggles, elastic, snaps, zippers, velcro, or any other suitable component present. This adjustable apparatus is implemented in an effort to tighten or loosen the band. The sleeve's specific measurement is determined by a person's weight, and which body part it is utilized. The presence of stitching or other suitable material and its sizing, style and location on a Barrier Band, will vary among the variations.

OBJECT OF THE INVENTION

It is an object of the present invention to protect the skin of someone who has a vascular access device and/or its components placed on any body part with a sleeve like apparatus. It is another object of the invention to protect such skin without dragging, snagging, pulling or otherwise interfering with the vascular access device and its components. A feature of this invention is that the sleeve is made from a single piece of washable or disposable material that is smooth on the inner and outer surface, includes an opening in the fore and aft ends, and contains a tunnel located at each end, which provides a barrier between the skin and the components of the vascular access device. In another embodiment stitching is present adjacent the aft and fore ends defining the tunnel. In another embodiment the embodiment is doubled layered and contains no stitching. The size or presence of stitching or any others means of adherence, and its positioning will vary among different embodiments. In another embodiment an adjustable apparatus (i.e. zips, hooks, toggles, elastic snaps, zippers etc.) or any other suitable adjustable apparatus component is present. This adjustable apparatus is implemented in an effort to tighten or loosen the band. Any sleeve's specific measurement choice is determined by a person's weight, and which body part it is covered.

BRIEF DESCRIPTION OF THE DRAWING

The present invention, in accordance with one or more various embodiments, is described in detail with reference to the following figures. The drawings are provided for purposes of illustration only and merely depict typical or example embodiments of the invention. In an effort to have the reader understand the invention and not to limit the breadth, scope, or applicability of the invention in any way, these drawings are provided. These drawings are not necessarily made to scale. Descriptive drawing terms illustrating various embodiment-viewing angles, such as "top," or "front" views are merely descriptive and do not imply or require that the invention be implemented or used in a particular spatial orientation unless explicitly stated otherwise.

FIG. 1 is a front and top view of the present invention with a tunnel containing a double stitched configuration.

FIG. 2 is a top view taken over line 1 of FIG. 1.

FIG. 3 is a front and top view of the present invention with a tunnel containing a double stitched configuration, featuring an adjustable apparatus;

FIG. 4 is a front view of the adjustable apparatus.

FIG. 5 is a top view taken over line 1 of FIG. 3.

FIG. 6 is a front and top view of the present invention with a tunnel containing a double stitched configuration featuring an adjustable hook apparatus.

FIG. 7 is a front view of the adjustable full hook apparatus.

FIG. 8 is a front view of the adjustable hook apparatus, as it would appear attached to the present invention.

FIG. 9 is a top view taken over line 1 of FIG. 6.

FIG. 12 is a front and top view of the present invention with two tunnel openings containing a single shortened stitch configuration.

FIG. 13 is a top view taken over line 1 of FIG. 12.

FIG. 14 is a front and top view of the present invention with two tunnel openings, containing a no stitch configuration.

FIG. 15 is a top view taken over line 1 of FIG. 14.

FIG. 16 is a cut-through view of the present invention with a curved tunnel entry point.

FIG. 17 is a cut-through view of the present invention with a flat tunnel entry point.

FIG. 18 is a front and top view of the present invention in an opened version containing a foldable tunnel and foldable band configuration.

FIG. 19 is a side view taken over line 1 of FIG. 18.

FIG. 20 is a cut through view of line 1 of FIG. 18.

FIG. 21 is another perspective view of the invention positioned over a hand.

FIG. 22 is another perspective view of the invention positioned over a foot.

FIG. 23 is another perspective view of the invention positioned over an ankle.

FIG. 24 is another perspective view of the invention positioned over a neck.

FIG. 25 is another perspective view of the invention positioned over a head.

FIG. 26 is another perspective view of the invention positioned over an arm.

FIG. 27 is another perspective view of the invention positioned over a chest.

FIG. 28 is another perspective view of the invention positioned over a leg.

DETAILED DESCRIPTION OF THE PREFERRED EMBODIMENTS

Figures 10, 11:
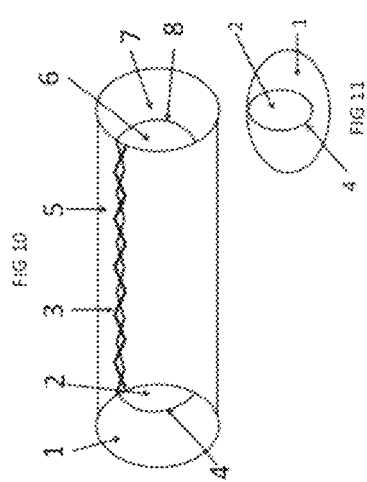
FIG. 10 is a front and top view of the present invention with two tunnel openings containing a single stitch configuration.
FIG. 11 is a top view taken over line 1 of FIG. 10.

Various embodiments are now described with reference to the drawings, wherein like reference numerals are used to refer to like elements throughout. In the following description, for purposes of explanation, specific details are set forth in order to provide a thorough understanding of one or more embodiments. It may be evident, however, that such embodiment(s) may be practiced without these specific details and be practiced with modification within the spirit and cope of the appended claims. The present invention is directed toward a sleeve that covers a person's vascular access device area on their body, while simultaneously protecting their skin with a tunnel. When a patient has any type of vascular access device it is covered with medical grade disposable gauze, netting, or other suitable material. It can also be covered in a washable spandex, polyester, or other suitable material. This is to keep it protected and secure. A problem that many patients have when they are required to wear this cover is that their skin becomes irritated as a result of the cover causing the vascular access device and its components to press against the skin. Consequently, whether it is short or long-term use, the skin should be protected during its use, and no current invention provides a barrier between the skin and vascular access device and its components, like the present invention does. At times patients that need this device already have comprised skin, which means it will be further comprised. This complete coverage fully eliminates all discomfort. The sleeve's specific measurement and configuration is determined by a person's weight, and which body part it is utilized. A common complaint amount people are that with extended use, a cover of this type does not work effectively. For that reason, some washable variations of the Barrier Band have an adjustable apparatus including: zips, hooks, toggles, elastic, snaps, zippers, velcro, or any other suitable component present. This adjustable apparatus is implemented in an effort to tighten or loosen the band. The disposable version is made with a specific tubular netting to accommodate a patient's needs.

FIG. 1 Illustrates a sleeve (5) for a vascular access device site. Such a site can be present on several different body parts. The sleeve (5) can be placed on a body part through the open ends (1) and (8), and the sleeve's specific measurement is determined by a patient's size, and which body part it is being covered. This is a front and top view of the present invention featuring a tunnel opening (2) and (6) that creates a barrier (4) and (8) between a person's vascular access device and their skin. This embodiment contains a double stitch (3) configuration.

FIG. 2 Is a top view taken over line 1 of FIG. 1. It illustrates an opening (1) for a body part, the tunnel (2) where the vascular access device components are placed, and the actual barrier (4) provided by the Barrier Band, in between the body part and the vascular access device, and its components.

FIG. 3 Illustrates a sleeve (5) for a vascular access device site. Such a site can be present on several different body parts. The sleeve (5) can be placed on a body part through the open ends (1) and (8), and the sleeve's specific measurement is determined by a patient's size, and which body part it is being covered. This is a front and top view of the present invention featuring a tunnel opening (2) and (6) that creates a barrier (4) and (8) between a person's vascular access device and their skin. This embodiment contains a double stitch (3) configuration, and features an adjustable apparatus (9), in the form of a elastic pull string, which is inserted to enable someone to tighten or loosen his or her band. FIG. 4 is a front view of the adjustable apparatus (9), which is inserted to enable someone to tighten or loosen their band. FIG. 5 is a top view taken over line 1 of FIG. 3. It illustrates an opening (1) for a body part, the tunnel (2)

where the vascular access device components are placed and the actual barrier (4) in between the body part and the vascular access device, and its components. It also features an adjustable apparatus (9), in the form of elastic, which is inserted to enable someone to tighten or loosen his or her band.

FIG. 6 Illustrates a sleeve (5) for a vascular access device site. Such a site can be present on several different body parts. The band (5) can be placed on a body part through the open ends (1) and (8), and the sleeve's specific measurement is determined by a patient's size, and which body part it is being covered. This is a front and top view of the present invention featuring a tunnel opening (2) and (6) that creates a barrier (4) and (8) between a person's vascular access device and their skin. This embodiment contains a double stitch (3) configuration, and features an adjustable apparatus (10) in the form of a hook, which is inserted to enable someone to tighten or loosen their band.

FIG. 7 is a front view of the adjustable full hook apparatus. This is the hook in its full form before it is adhered to the band (5).

FIG. 8 is a front view of the adjustable hook apparatus, as it would appear when it is attached to the present invention.

FIG. 9 is a top view taken over line 1 of FIG. 6. It illustrates an opening (1) for a body part, the tunnel (2) where the vascular access device components are placed and the actual barrier (4) in between the body part and the vascular access device, and its components. It also features an adjustable apparatus (9), in the form of a hook, which is inserted to enable someone to tighten or loosen their band.

FIG. 10 Illustrates a band (5) for a vascular access device site. Such a site can be present on several different body parts. The band (5) can be placed on a body part through the open ends (1) and (8), and the band's specific measurement is determined by a patient's size, and which body part it is being covered. This is a front and top view of the present invention featuring a tunnel opening (2) and (6) that creates a barrier (4) and (8) between a person's vascular access device and their skin. This embodiment contains a single stitch (3) configuration.

FIG. 11 Is a top view taken over line 1 of FIG. 10. It illustrates an opening (1) for a body part, the tunnel (2) where the vascular access device components are placed, and the actual barrier (4) provided by the Barrier Band, in between the body part and the vascular access device, and its components.

FIG. 12 Illustrates a sleeve (5) for a vascular access device site. Such a site can be present on several different body parts. The sleeve (5) can be placed on a body part through the open ends (1) and (8), and the sleeve's specific measurement is determined by a patient's size, and which body part it is being covered. This is a front and top view of the present invention featuring a tunnel opening (2) and (6) that creates a barrier (4) and (8) between a person's vascular access device and their skin. This embodiment contains a shortened single stitch (3) configuration.

FIG. 13 Is a top view taken over line 1 of FIG. 12. It illustrates an opening (1) for a body part, the tunnel (2) where the vascular access device components are placed, and the actual barrier (4) provided by the Barrier Band, in between the body part and the vascular access device, and its components.

FIG. 14 Illustrates a sleeve (5) for a vascular access device site. Such a site can be present on several different body parts. The sleeve (5) can be placed on a body part through the open ends (1) and (7), and the sleeve's specific measurement is determined by a patient's size, and which body part it is being covered. This is a front and top view of the present invention featuring a tunnel opening (2) and (6) that creates a barrier (4) and (8) between a person's vascular access device and their skin. This embodiment contains no stitch.

FIG. 15 Is a top view taken over line 1 of FIG. 14. It illustrates an opening (1) for a body part, the tunnel (2) where the vascular access device components are placed, and the actual barrier (4) provided by the Barrier Band, in between the body part and the vascular access device, and its components.

FIG. 16 is a cut-through view of the present invention showing the access point for a body part (1) with a curved tunnel entry point (4), stitching (3), and a open view of the barrier (2).

FIG. 17 is a cut-through view of the present invention showing the access point for a body part (1) with a flat tunnel entry point (4), stitching (3), and a open view of the barrier (2).

FIG. 18 is a is a front and top view of the present invention, where the sleeve (4) is offered in an opened version configuration, containing a foldable ductway (3) and the band (4) can be folded over a body part. In this embodiment, the body part is placed on one side (1) of the tunnel, and the components of the vascular access device are placed on the other side (2) of the tunnel.

FIG. 19 is a side view taken over line 1 of FIG. 18 of the present invention, where the sleeve (4) is offered in an opened version configuration, containing a foldable tunnel (3) and the sleeve (4) can be folded over a body part. In this embodiment, the body part is placed on one side (1) of the tunnel, and the components of the vascular access device are placed on the other side (2) of the tunnel.

FIG. 20 is a cut through view of line 1 of FIG. 18 of the present invention, where the sleeve (4) is offered in an opened version configuration, containing a foldable tunnel (3) and the sleeve (4) can be folded over a body part. In this embodiment, the body part is placed on one side (1) of the tunnel, and the components of the vascular access device are placed on the other side (2) of the tunnel.

FIG. 21 is another perspective view of the invention in use and positioned over a hand.

FIG. 22 is another perspective view of the invention in use and positioned over a foot.

FIG. 23 is another perspective view of the invention in use and positioned over a ankle.

FIG. 24 is another perspective view of the invention in use and positioned over a neck.

FIG. 25 is another perspective view of the invention in use and positioned over a head.

FIG. 26 is another perspective view of the invention in use and positioned over a arm.

FIG. 27 is another perspective view of the invention in use and positioned over a chest.

FIG. 28 is another perspective view of the invention in use and positioned over a leg.

The body parts listed and illustrated in FIGS. 21 through 28, are for the intent to provide an understanding of the invention's purpose, and not to limit its use on those body parts only. As illustrated and described above, through the several embodiments offered, there are many effective ways to implement the barrier's method of use regardless of a person's weight or what body part needs to be covered.

I claim:

1. An apparatus consisting, essentially of:
 a sleeve including:
 a main body having a first portion and a second portion. said main body comprising a tubular, breathable, netting material that is configured to stretch to fit differently sized body pails, said main body including a first open end and a second open end; and
 a tunnel configured to receive vascular access device components, wherein the tunnel is formed on an interior of the sleeve, said tunnel comprising a breathable, netting material,
 wherein the tunnel is fixed to the sleeve with two rows of stitching,
 wherein a first portion of said main body is configured to form around a human body part at said first open end of said main body,
 wherein a second portion of said main body is configured to form around a human body part at said second open end of said main body, and
 wherein a first tunnel opening is integrally formed at said first open end and a second tunnel opening is integrally formed at said second open end.

2. The apparatus of claim 1, wherein said two rows of stitching include a first row of stitching on a first lateral side of the tunnel running along the length of the sleeve and a second row of stitching at a second lateral side of the tunnel running along the length of the sleeve.

3. The apparatus of claim 1, wherein a portion of said stitching is defined with a color.

4. The apparatus of claim 1, wherein a circumference of said first open end of the main body is not equal to a circumference of said second open end of the main body.

5. The apparatus of claim 1, wherein said sleeve further comprises a size adjusting device.

6. The apparatus of claim 5, wherein said size adjusting device is a hook.

7. The apparatus of claim 5, wherein said size adjusting device is elastic.

8. The apparatus of claim 1, where said netting material of said main body and said netting material of said tunnel includes at least one color or a pattern.

9. The apparatus of claim 1, wherein said sleeve has a colored area.

10. The apparatus of claim 1, wherein said first tunnel opening has an inward curvature in a direction parallel to the length of the sleeve.

11. The apparatus of claim 1, wherein said first tunnel opening and said second tunnel opening each form a straight line in a direction perpendicular to the length of the sleeve.

12. The apparatus of claim 1, wherein said tunnel is configured to receive an attachable component.

13. A method of protecting the skin on any section of a human body with the apparatus of claim 1, comprising the steps of:
 placing the sleeve on a body part of a person having a vascular access device area;
 adjusting said sleeve up to the vascular device access area;
 placing vascular device access components into the tunnel;
 tucking the vascular device access components hack up through the bottom of the tunnel, if needed; and
 moving one of the first open end of the main body or the second open end of the main body thereby covering said vascular device access area entirely.

14. The apparatus of claim 1, wherein a circumference of said first open end of the main body is equal to a circumference of said second open end of the main body.

15. An apparatus consisting essentially of:
 a sleeve including:
 a main body having a first portion and a second portion, said main body comprising a tubular, breathable material that is configured to stretch to fit differently sized body parts, said main body including a first open end and a second open end,
 wherein a circumference of said first open end of the main body is not equal to a circumference of said second open end of the main body,
 wherein the main body consists of a single piece of washable material that is smooth on an inner surface and an outer surface of the main body;
 wherein one of the first open end and the second open end includes an adjustable elastic pull string which is configured to be tightened or loosened with a toggle; and
 a tunnel configured to receive vascular access device components, wherein the tunnel is formed on an interior of the sleeve, said tunnel comprising a breathable material,
 wherein the tunnel is fixed to the sleeve with two rows of stitching,
 wherein a first portion of said main body is configured to form around a human body part at said first open end of said main body,
 wherein a second portion of said main body is configured to form around a human body part at said second open end of said main body,
 wherein a first tunnel opening is integrally formed at said first open end and a second tunnel opening is integrally formed at said second open end, and
 wherein said first tunnel opening has an inward curvature in a direction parallel to the length of the sleeve.

* * * * *